(12) United States Patent
Melkent

(10) Patent No.: US 8,262,738 B2
(45) Date of Patent: Sep. 11, 2012

(54) VERTEBRAL IMPLANT CONTAINMENT DEVICE AND METHODS OF USE

(75) Inventor: Anthony J. Melkent, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 124 days.

(21) Appl. No.: 12/971,426

(22) Filed: Dec. 17, 2010

(65) Prior Publication Data
US 2011/0087330 A1  Apr. 14, 2011

Related U.S. Application Data

(63) Continuation of application No. 11/610,520, filed on Dec. 14, 2006, now Pat. No. 7,875,079.

(51) Int. Cl.
*A61F 2/44* (2006.01)
(52) U.S. Cl. ............... 623/17.16; 623/17.15; 606/246
(58) Field of Classification Search ............. 606/86 A, 606/90, 246, 249; 623/17.11–17.16
See application file for complete search history.

(56) References Cited

U.S. PATENT DOCUMENTS
8,083,800 B2 * 12/2011 Edie ..................... 623/17.16
* cited by examiner

*Primary Examiner* — Kevin T Truong
*Assistant Examiner* — Larry E Waggle, Jr.

(57) ABSTRACT

A containment device is inserted between vertebral members in a patient and provides a rapid implant solution adapted for use in different applications. The device includes an interior volume to contain a curable substance at substantially atmospheric pressure. Upon filling the enclosure member with a curable substance, the enclosure member is able to conform to and maintain a space between vertebral members. The containment device may include an enclosure member constructed of an impermeable material adapted to constrain migration of the curable substance. The enclosure member may include an exterior wall surrounding the interior volume and an opening in the exterior wall that exposes the interior volume. The containment device may include end members that may be distracted to establish a desired vertebral spacing. Spacer members may be included to further maintain the desired spacing. Upon hardening of the curable substance, the device is capable of maintaining the desired spacing.

17 Claims, 6 Drawing Sheets

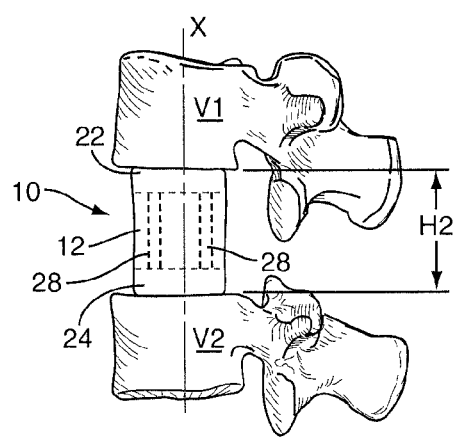
FIG. 12
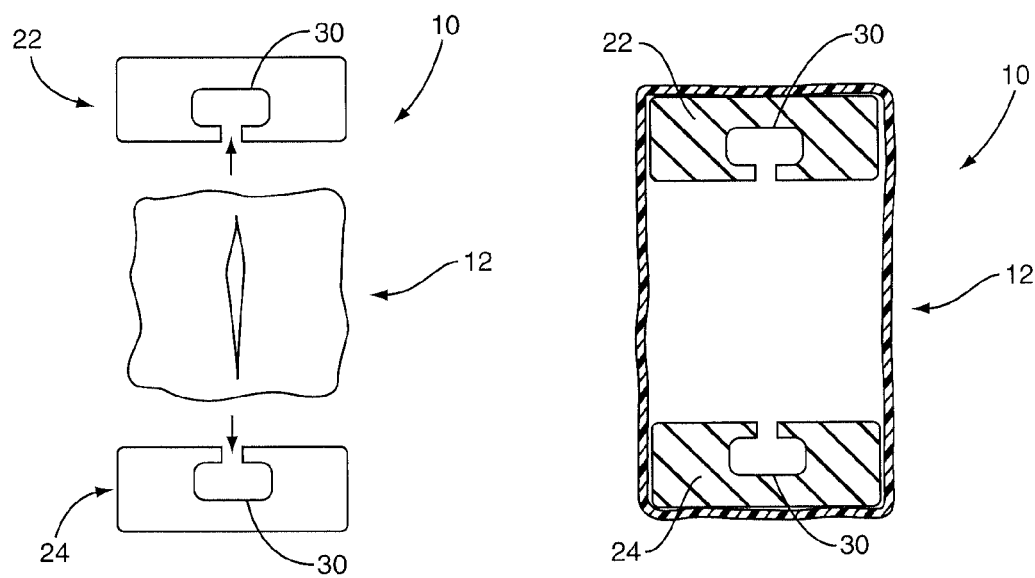
FIG. 13  FIG. 14

VERTEBRAL IMPLANT CONTAINMENT DEVICE AND METHODS OF USE

RELATED APPLICATION

This application is a continuation of U.S. patent application Ser. No. 11/610,520, filed on Dec. 14, 2006, and incorporated in its entirety herein by reference.

BACKGROUND

Spinal implants are often used in the surgical treatment of spinal disorders such as degenerative disc disease, tumors, disc herniations, scoliosis or other curvature abnormalities, and fractures. Many different types of treatments are used, including the removal of one or more vertebral bodies and/or intervertebral disc tissue. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies. Regardless of the type of treatment and the type of implant used, surgical implantation tends to be difficult for several reasons. For instance, access to the affected area may be limited by other anatomy. Further, a surgeon must be mindful of the spinal cord and neighboring nerve system.

In some applications, surgeons may wish to use a curing substance in lieu of more expensive and complex devices as a rapid vertebral body replacement. Unfortunately, these curing substances tend to be fluid or malleable in nature prior to curing and consequently tend to migrate in the absence of a containment device. Accordingly, a containment device may be appropriate for use in these applications to control the migration of curable substances prior to hardening.

SUMMARY

Illustrative embodiments disclosed herein are directed to a containment device that is insertable between vertebral members in a patient. The containment device may provide a rapid, cost-effective implant solution adapted for use in different applications.

The device may includes first and second end members each including a first side and an opposing second side. The device may also include an enclosure member that extends around and is attached to each of the first and second end members and forms an interior volume between the end members. The first end member may be attached to the enclosure member at a first location and the second end member may be attached to the enclosure member at a second location that is spaced apart from the first location. The second sides of the first and second end members may face into the interior volume. The first and second end members may be positioned within the enclosure member and may be spaced from the vertebral members by the enclosure member when the containment device is inserted between the vertebral members. The enclosure member may be positionable between a first orientation with the first and second end members in closer proximity and the interior volume being smaller, and a second orientation with the first and second end members spaced a farther distance apart and the interior volume being larger. The first and second end members may each be attached to the enclosure member and move apart when the enclosure member moves from the first orientation to the second orientation.

The device may include first and second end members each including a first side and an opposing second side. An enclosure member may extend around each of the first and second end members and form an enclosed interior volume between the end members. Engagement features may be positioned on the second sides of the first and second end members and may be configured to receive a tool. The engagement features may be surrounded by the enclosure member and exposed in the interior volume. An opening in the enclosure member may extends into the interior volume and may be positioned between the first and second end members and in proximity to the engagement features. The enclosure member may be positionable between a first orientation with the engagement features of the first and second end members in closer proximity and the interior volume being smaller, and a second orientation with the engagement features of the first and second end members spaced a farther distance apart and the interior volume being larger.

The device may include first and second end members each including a first side configured to contact one of the vertebral members and an opposing second side. An anchor recess may extend into the second side of the first end member. The anchor recess may include a narrow inlet at the second side that leads into an enlarged section positioned away from the second side. A flexible enclosure member may be attached to the second sides of each of the first and second end members and may form an enclosed interior volume between the end members. The enclosure member may be positionable between a first orientation with the first and second end members in closer proximity and the interior volume being smaller, and a second orientation with the first and second end members spaced a farther distance apart and the interior volume being larger. The enclosure member may be positioned away from the enlarged section of the anchor recess in the first orientation and positioned within the enlarged section of the anchor recess in the second orientation.

BRIEF DESCRIPTION OF THE DRAWINGS

FIGS. 10-12 illustrate a sequence of implantation steps to obtain a desired vertebral body spacing, each Figure depicting a lateral view of a containment device according to one or more embodiments shown relative to vertebral bodies;

FIG. 13 is a side view of a containment device including end members according to one embodiment; and FIG. 14 is a side view of a containment device including end members according to one embodiment.

DETAILED DESCRIPTION

Figure 1:
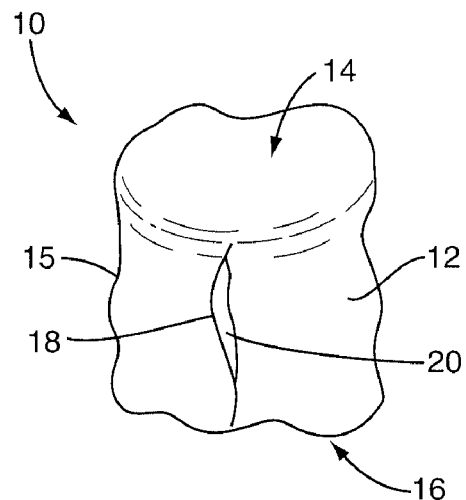
FIG. 1 is a perspective view of a containment device according to one embodiment.
Figure 2:
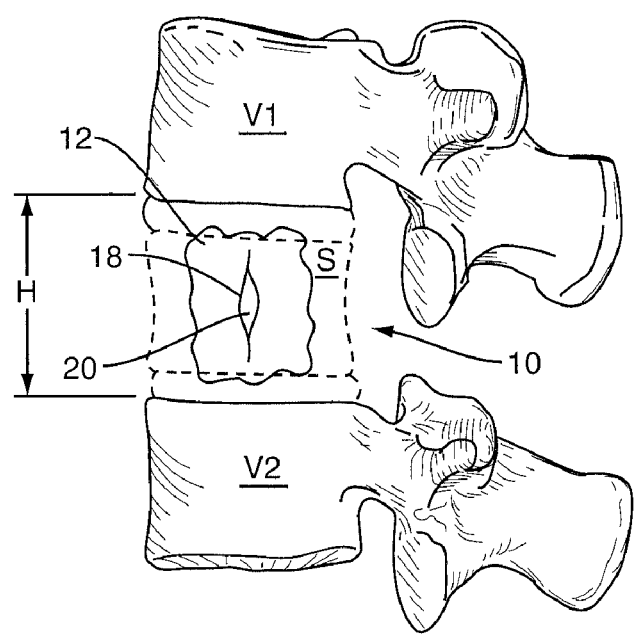
FIG. 2 is a side elevation view of an unfilled containment device according to one embodiment positioned between vertebral bodies.
Figure 3:
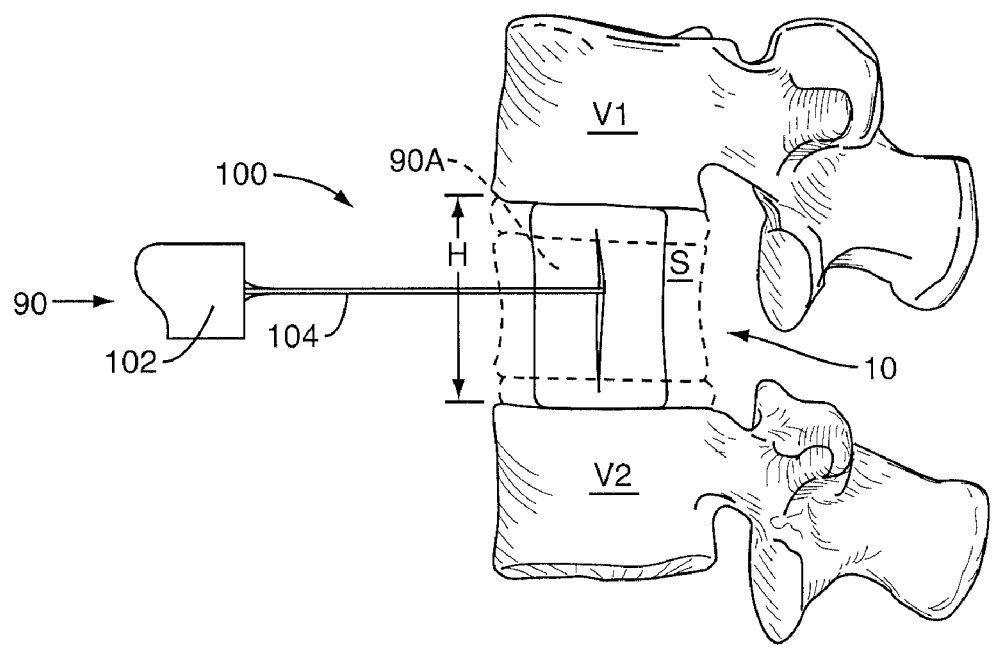
FIG. 3 is a side elevation view of a containment device according to one embodiment positioned between vertebral bodies and being filled.

The various embodiments disclosed herein are directed to vertebral implants that include a containment device within which a curable substance may be inserted. The containment device is generally a flexible, collapsible member that includes an interior volume that may contain the curable substance. The containment device may assume a compressed first state during installation of the containment device and may be filled with a curable liquid substance to assume a second filled state once the device is positioned within the body. An exemplary containment device 10 for supporting vertebral bodies is illustrated in FIG. 1. In one embodiment, the containment device 10 is a discectomy, vertebrectomy, or corpectomy implant positioned within an intervertebral space. The intervertebral space may span a single disc space or may span one or more vertebral levels along the longitudinal axis of the spinal column. For example, FIGS. 2 and 3 illustrate that the containment device 10 is positionable within an intervertebral space S to span one or more vertebral levels along the longitudinal axis of the spinal column. Although the illustrated embodiment of the implant 10 spans one vertebral level, it should be understood that the implant 10 may be configured to span multiple vertebral levels, including two or more vertebral levels.

In the illustrated embodiment, the containment device 10 includes a flexible enclosure member 12 that is constructed of a compliant biocompatible material, such as a resin or polymer that may include materials such as nylon, polyethylene, polyurethane, silicone, polyethylene, polypropylene, polyimide, polyamide, and polyetheretherketone (PEEK). The enclosure member 12 may be formed from materials that are used in other conventionally known biomedical applications, such as balloon angioplasty. Further, the enclosure member 12 may be reinforced with concentric layers of similar or dissimilar materials and/or fabrics (not specifically shown). For instance, a reinforcing structure may be constructed of a wide variety of woven or nonwoven fibers, fabrics, metal mesh such as woven or braided wires, polymeric fibers, ceramic fibers, and carbon fibers. Biocompatible fabrics or sheet material such as ePTFE and Dacron®, Spectra®, and/or Kevlar® brand materials may also be used. In general, the enclosure member 12 should be substantially impermeable with regards to a curable substance so that the curable substance remains confined to the containment device 10 and does not migrate to the patient by an excessive amount. That is, the enclosure member 12 may be entirely impermeable such that all of the curable substance remains within the enclosure member 12. Alternatively, as with woven fabrics, the enclosure member 12 may be slightly permeable such that some of the curable substance escapes the enclosure member without negative effect to the patient. As used herein, the term "impermeable" is intended to cover each of these variations (e.g., entirely or substantially impermeable).

The enclosure member 12 includes longitudinal ends 14, 16 that are positioned to engage vertebral members in use. The enclosure member 12 includes a lateral wall 15 extending between the longitudinal ends 14, 16. Further, the enclosure member 12 includes an opening 18 in the lateral wall 15 extending between the outside of the enclosure member 12 and an interior volume 20 that is formed between the ends 14, 16 and wall 15. The opening 18 is not necessarily a sealed opening capable of containing a curable substance at elevated pressures. Instead, the opening 18 provides access to the interior volume 20 to permit the enclosure member 12 to contain a curable substance at atmospheric pressure. Further, with the opening 18 facing upwards during surgery, the curable substance may be contained within the enclosure member 12 by gravity. Consequently, upon filling the enclosure member 12 with a curable substance, the enclosure member 12 is able to conform to a space within which the enclosure member 12 is confined. Then, upon hardening of the curable substance, the enclosure member 12 is capable of maintaining the inter-vertebral space and sustaining biomechanical loading.

For example, the enclosure member 12 is adapted to engage the endplates of upper and lower vertebral bodies V1, V2 as shown in FIGS. 2 and 3. The enclosure member 12 maintains an intervertebral axial space S between the upper and lower vertebral bodies V1, V2 following the removal of one or more vertebral levels (shown in phantom in FIGS. 2 and 3). To facilitate insertion of the containment device 10, the enclosure member 12 may be collapsed relative to a filled state as shown in FIG. 2. The enclosure member 12 is compressed to fit between the vertebral bodies V1, V2, which are spaced apart a distance H. The opening 18 into the interior volume 20 is laterally accessible in this state. Once the containment device 10 is positioned as shown in FIG. 2, an insertion instrument 100 is used to introduce a curable substance 90 through the opening 18 and into the interior volume 20 of the enclosure member 12 as shown in FIG. 3.

The insertion instrument 100 may be implemented as a syringe-like structure including a reservoir portion 102 and a delivery portion 104. The delivery portion 104 is configured to pass through the opening 18 to transfer the injectable substance from the reservoir portion 102 into the interior volume 20 of the enclosure member 12. Other delivery mechanisms are certainly appropriate. For instance, pneumatic or hydraulic delivery systems may be appropriate. In other implementations, the curable substance 90 may include a malleable form, such as a thickened paste, or clay-like consistency. Accordingly, the insertion instrument 100 may comprise a scoop, blade, or other delivery instrument for inserting the curable substance 90. In other embodiments, the curable substance 90 may be inserted manually (e.g., by hand) into the enclosure member 12. For more fluid curable substances 90, the delivery portion 104 may be implemented as a needle, as tubing, or other cannulated devices. In any event, as the injectable substance is introduced into the enclosure member 12, longitudinal ends 14, 16 are forced apart due to the expansion of the enclosure member 12. Ultimately, the containment device 10 assumes a filled second state that spans the vertebral gap H as shown in FIG. 3. Notably, the vertebral gap H is substantially the same before and after filling the interior volume 20 of the enclosure member 12, suggesting that the containment device 10 is not intended to distract the vertebral bodies V1, V2. Instead, the containment device 10 is intended to fill the vertebral gap H using a simple device that confines a curable substance 90 to the space S between the vertebral bodies V1, V2.

A variety of curable substances 90 may be inserted into the enclosure member 12. In one embodiment, the curable substance fluid, liquid, gas, or solid (e.g., powder or granules) that hardens to a more rigid state after a predetermined amount of time or under the influence of an external catalyst. For instance, a curable substance 90 may cure under the influence of heat or light, including ultraviolet light. Some examples of in situ curable liquids include epoxy, PMMA, polyurethane, and silicone. The curable substance 90 may assume a first state 90 during insertion and assume a second state 90A after insertion into the interior volume 20 of the enclosure member 12. For example, the curable substance 90 in the first state may be fluid to facilitate insertion. Then, the curable substance 90A may cure to a substantially rigid state or to a flexible, but relatively incompressible state.

In the illustrated embodiment, enclosure member 12 includes a cylindrical shape, though other shapes may be used. In further embodiments, the enclosure member 12 may take on other types of configurations, such as, for example, a circular shape, semi-oval shape, bean-shape, D-shape, elliptical-shape, egg-shape, or any other shape that would occur to one of skill in the art. In other embodiments, the enclosure member 12 could also be described as being annular, U-shaped, C-shaped, V-shaped, horseshoe-shaped, semi-circular shaped, semi-oval shaped, or other similar terms defining an implant including at least a partially open or hollow construction. Thus, the enclosure member 12 may be constructed for use in a variety of procedures, including but not limited to those requiring an anterior approach, a lateral approach, a posterior approach, or a trans-foraminal approach.

It should further be appreciated that the size and/or configuration of the enclosure member 12 may be specifically designed to accommodate a particular region of the spinal column and/or a particular vertebral level. For example, in embodiments associated with the upper thoracic or cervical region of the spine, the enclosure member 12 may be designed to have a D-shaped configuration, whereas embodiments associated with the lumbar region of the spine may be configured to have a cylindrical, horseshoe-shape, a U-shape, or other types of open-sided configurations.

Figure 4:
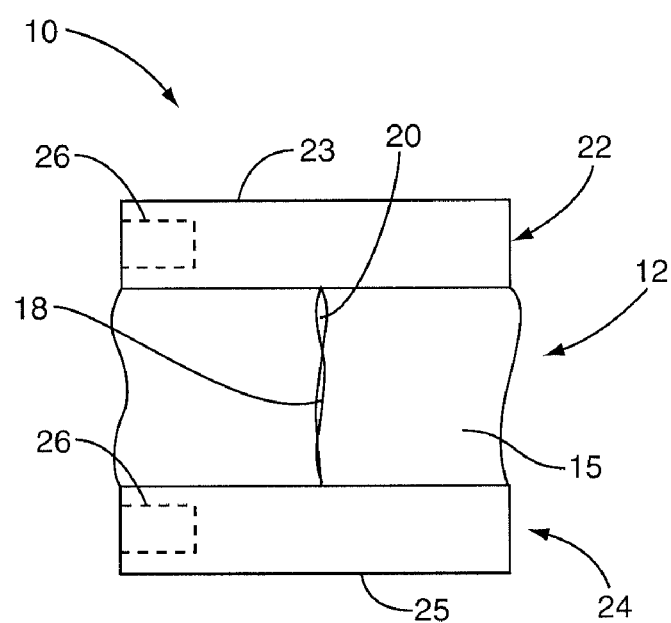
FIG. 4 is a side view of a containment device including end members according to one embodiment.
Figure 5:
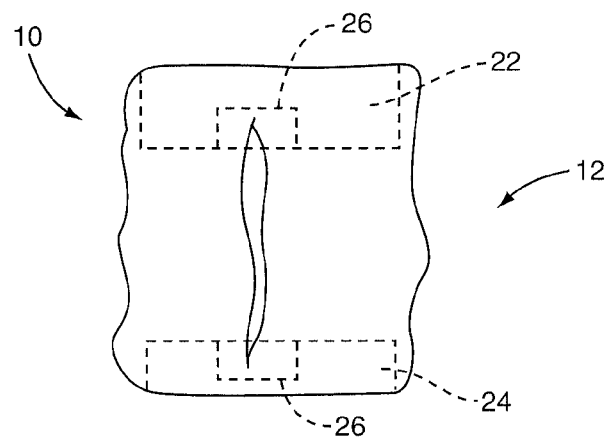
FIG. 5 is a side view of a containment device including end members according to one embodiment.

In the embodiment shown in FIGS. 1-3, the containment device 10 includes primarily an enclosure member 12 within which a curable substance 90 is inserted. Thus, substantially the entire containment device 10 is flexible and implant rigidity is derived from the curable substance 90. In FIG. 4, the containment device 10 includes a first end member 22, a second end member 24, and an enclosure member 12 between the first and second end members 22, 24. The end members 22, 24 are adapted to engage the endplates of upper and lower vertebral bodies V1, V2. In this particular embodiment, the enclosure member 12 is confined to the space between the end members 22, 24 and does not directly contact the vertebral bodies V1, V2. In FIG. 5, the containment device 10 includes first 22 and second 24 end members that are contained within the interior volume 20 of the enclosure member 12. Since the end members 22, 24 are contained within the enclosure member in this particular embodiment, the enclosure member 12 contacts the vertebral bodies V1, V2. In one embodiment, the end members 22, 24 are formed of a biocompatible material, such as, for example, a carbon fiber material, or non-metallic substances, including polymers or copolymers made from materials such as PEEK and UHMWPE. In further embodiments, the end members 22, 24 may be formed of other suitable biocompatible materials including metals, such as, for example, stainless steel, titanium, cobalt-chrome, or shape memory alloys. In one embodiment, the end members 22, 24 are coupled to the enclosure member 12. In one embodiment, the end members 22, 24 are separable from the enclosure member 12.

In the embodiment shown in FIG. 4, the end members 22, 24 directly contact the vertebral bodies V1, V2. The bone contact surfaces 23, 25 of the end members 22, 24 may include surface geometry, coating, or porosity as are found in conventionally known vertebral implants. Surface features such as these are used to promote bone growth and adhesion at the interface between an implant and a vertebral end plate. Examples of features used for this purpose include, for example, teeth, scales, keels, knurls, and roughened surfaces. Some of these features may be applied through post-processing techniques such as blasting, chemical etching, and coating, such as with hydroxyapatite. The bone interface surfaces 23, 25 may also include growth-promoting additives such as bone graft, bone morphogenetic protein (BMP), allograft, autograft, and various types of cement, growth factors, and mineralization proteins. Alternatively, pores, cavities, or other recesses into which bone may grow may be incorporated via a molding process. Other types of coatings or surface preparation may be used to improve bone growth into or through the bone-contact surfaces 23, 25.

Figure 6:
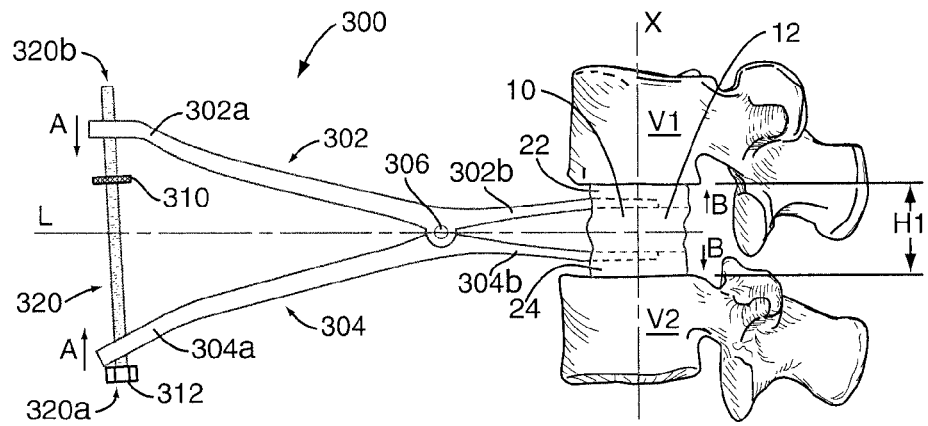
FIGS. 6-8 illustrate a sequence of implantation steps to obtain a desired vertebral body spacing, each Figure depicting a lateral view of a containment device according to one or more embodiments shown relative to vertebral bodies.
Figure 7:
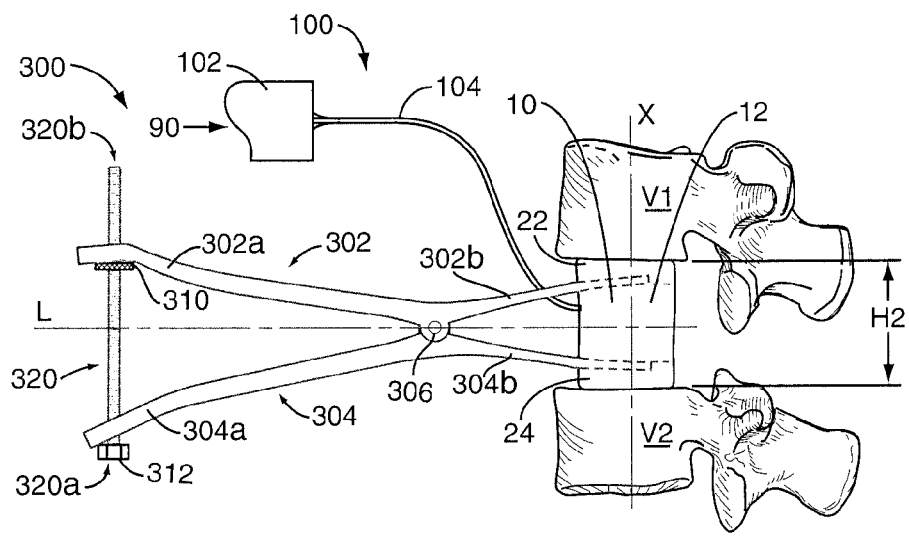
Figure 8:
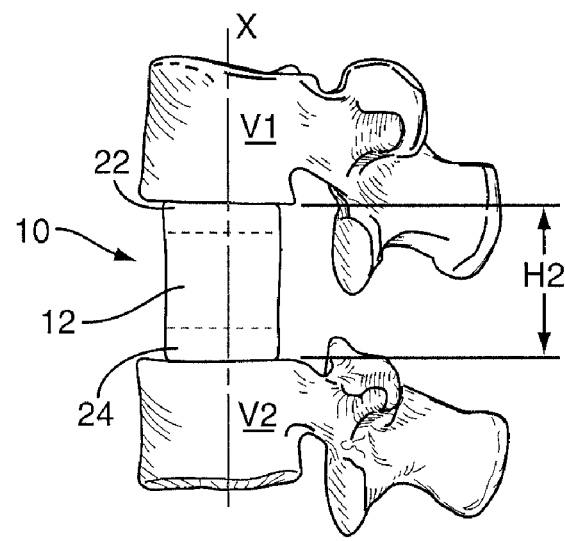

The end members 22, 24 for either embodiment (FIG. 4 or 5) include a distractor engagement feature 26. The distractor engagement feature 26 is included in the various embodiments as a means of achieving a desired vertebral spacing between vertebral bodies V1, V2 that is subsequently maintained by inserting the curable substance 90 into the interior volume 20 of the enclosure member 12 and allowing the curable substance 90 to harden. FIGS. 6-8 depict exemplary process steps by which the containment device 10 of FIG. 5 may be implanted. These same process steps may be followed to implant the containment device 10 of FIG. 4.

In FIG. 6, the containment device 10, including end members 22, 24, is inserted and positioned within an intervertebral space formed after the removal of one or more vertebrae or discs. The containment device 10 is positioned with the aid of a distractor 300 that engages the respective distractor engagement features 26 in the end members 22, 24. The exemplary distractor 300 extends along a longitudinal axis L and generally includes a first distractor arm 302 and a second distractor arm 304. The first and second distractor arms 302, 304 are coupled to one another via a hinge mechanism 306 which provides for pivotal movement between the distractor arms 302, 304 about the hinge mechanism 306. As should be appreciated, an inward compression force exerted onto the proximal portions 302a, 304a of the distractor arms in the direction of arrows A will cause the distal end portions 302b, 304b to be outwardly displaced in the direction of arrows B. Thus, distraction of the vertebral bodies V1, V2 is achieved along longitudinal axis X, which corresponds at least generally with the longitudinal axis of the spine and of the containment device 10.

In the illustrated embodiment, the distractor 300 includes a threaded rod 320 having a first end portion 320a rotatably coupled with the proximal end portion 304a of the distractor arm 304, and a second end portion 320b engaged within a threaded aperture (not specifically shown) extending through the proximal end portion 302a of the distractor arm 302. As should be appreciated, the position of rod 320 may be adjusted relative to the distractor arm 302 by threading the rod 320 with a rotary knob 312 to correspondingly control the amount of distraction provided by the distractor arms 302, 304. In one embodiment, the distractor 300 is provided with a gauge or stop member 310 that is adapted to limit outward displacement of the distal end portion 302b, 304b, which in turn correspondingly limits that amount of distraction provided by the distractor arms 302, 304. In this manner, over distraction of the intervertebral space S is avoided.

Figure 10:
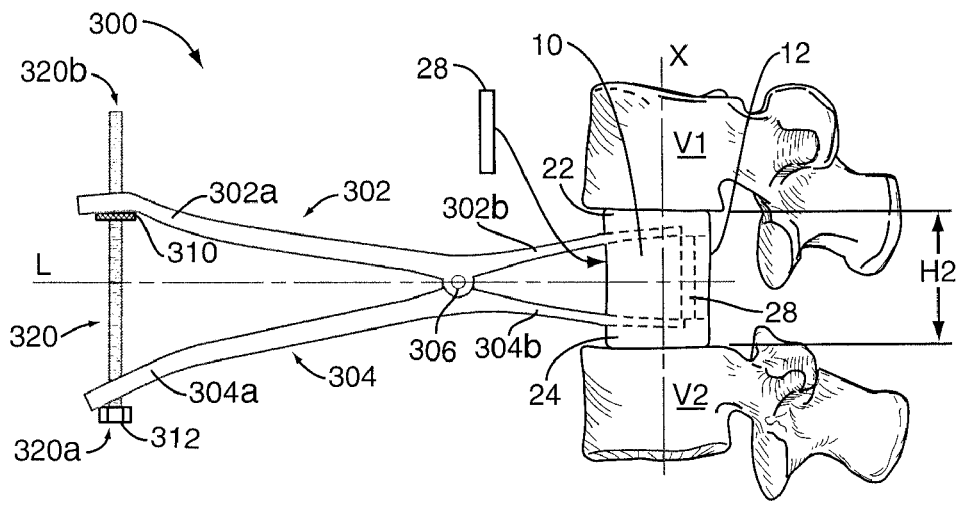

The distal end of the distal end portions 302b, 304b include geometry that engages the distractor engagement features 26 of the end members 22, 24. Notably, FIGS. 6, 7, and 10 illustrate one particular type of distractor 300 that uses a threaded rod 320 to achieve a mechanical advantage and distract the vertebral bodies V1, V2 a desired amount. However, those skilled in the art will appreciate that different types of distractors may be used, including but not limited to devices incorporating pneumatic, hydraulic, electrical, or mechanical displacement forces. However, it is generally contemplated that the distractor (300 or otherwise) include engaging features with a size and shape that engages the distractor engagement features 26, yet provides access to the enclosure member 12 while the distractor 300 is engaged with the distractor engagement features 26 as described herein.

With the distractor 300 engaged in the distractor engagement features 26 as shown in FIG. 6, the rotary knob 312 may be rotated to force the distal end portions 302b, 304b in the direction of arrows B. FIG. 7 shows the proximal ends 302a, 304a in closer proximity to one another. Correspondingly, the distal ends 302b, 304b are spaced farther apart compared to the position shown in FIG. 7. That is, the vertebral spacing H1 from FIG. 6 is increased to a greater distance H2 in FIG. 7. Once the desired amount of distraction is achieved, an insertion instrument 100 is used to introduce a curable substance 90 into the interior volume 20 of the enclosure member 12 as shown in FIG. 7 or using other techniques described herein. Once the curable substance 90 is allowed to cure or harden, the distractor 300 is removed, leaving the containment device 10 positioned to maintain the desired spacing H2 between vertebral bodies V1, V2 as shown in FIG. 8.

Figure 9:
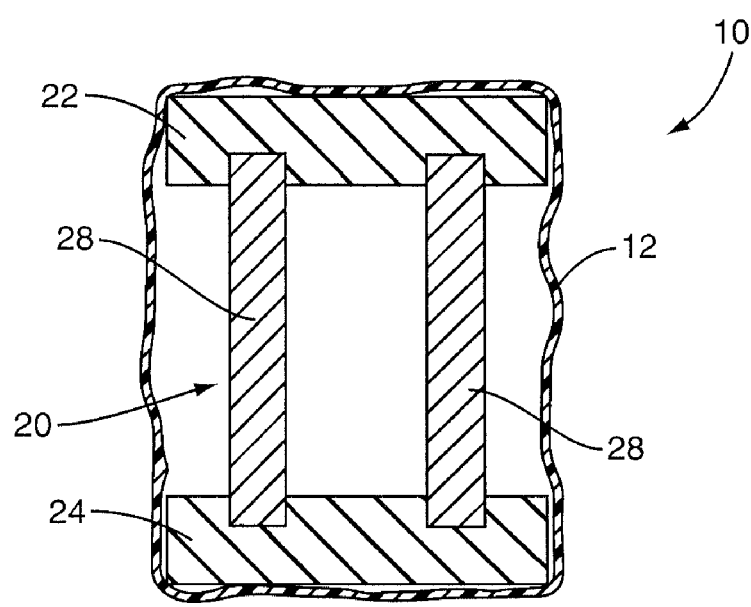
FIG. 9 is a side section view of a containment device including end members and spacer members according to one embodiment.

FIG. 9 depicts a side section view of one embodiment of a containment device 10 that includes spacer members 28. That is, the implant 10 generally includes a first end member 22 and a second end member 24 as described above, and one or more spacer members 28 coupled between the first and second end members 22, 24. The spacer members 28 are formed of a biocompatible material that may be the same or different that the end members 22, 24. For example, the spacer members may include a material that is less or more flexible than that of the end members 22, 24. In one embodiment, the spacer members 28 are sufficiently strong to maintain a desired amount of vertebral distraction while a curable substance 90 is inserted into the interior volume 20 of the enclosure member 12 and allowed to harden. Once the curable substance 90 hardens, the composite structure formed by the curable substance 90 and the spacer members 28 should be sufficient to maintain the desired vertebral spacing in the patient.

Figure 11:
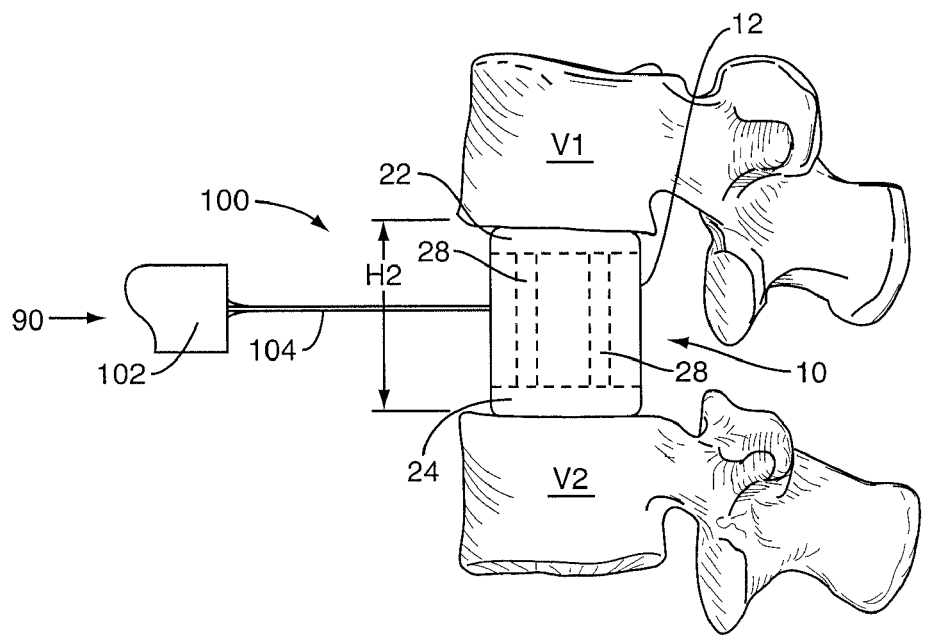

The spacer members 28 may be separate from the end members 22, 24. To facilitate insertion of the implant 10, the spacer member 28 may be inserted into a patient separately from the end members 22, 24. That is, the end members 22, 24 may be inserted during a first insertion step and the spacer member 28 may be inserted during a second, subsequent insertion step. Depending upon a surgeon's preferences, the spacer members 28 may be inserted between the end members 22,24 at different times of an implantation procedure. The process steps illustrated in FIGS. 10-12 show one exemplary method of inserting the spacer members 28. In one implementation, the containment device 10 may be inserted into the space S between vertebral bodies V1, V2 as shown in FIG. 6. Then, once a desired amount of distraction (spacing H2) is obtained, the spacers members 28 may be positioned between the end plates 22,24 as shown in FIG. 10. Once the one or more spacer members 28 are positioned as desired, the distractor 300 may be removed, leaving the spacer members 28 to maintain the desired distraction. Next, an injection instrument 100 is used to introduce a curable substance 90 into the interior volume 20 of the enclosure member 12 as shown in FIG. 11. The curable substance 90 is allowed to harden and the containment device 10 maintains the desired spacing H2 between vertebral bodies V1, V2 as shown in FIG. 12. Notably, the distractor 300 has already been removed at this stage, thus providing easier access to the enclosure members 12 and eliminating the need to maintain the desired distraction while the curable substance 90 hardens. Thus, the spacer members 28 may improve the ease with which the curable substance 90 is introduced to the enclosure member and reduce the overall the time required for the procedure.

FIGS. 13 and 14 illustrate that the end members 22, 24 may include anchor recesses 30 that improve the interface at each end member 22, 24. In FIG. 13, the end members 22, 24 are shown separated from the enclosure member 12. Each end member 22, 24 includes an anchor recess 30 that is sized and positioned to allow the enclosure member 12 to expand therein. Thus, as the enclosure member 12 is filled with the curable substance 90, the enclosure member 12 may expand or extend into the anchor recess 30. As the curable substance 90 hardens, the enclosure member 12 may be secured to the end members 22, 24.

Similarly, FIG. 14 depicts an embodiment in which the end members 22, 24 are contained within the enclosure member 12. In this particular embodiment, the end members 22, 24 include recesses that are sized and positioned to allow the curable substance 90 to expand therein. Thus, as the enclosure member 12 is filled with the curable substance 90, the curable substance expands or extends into the anchor recesses 30. Then, the curable substance 90 hardens to a more rigid state that is secured to the end members 22, 24.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the embodiments disclosed herein have contemplated a single implant positioned between vertebral bodies V1, V2. In other embodiments, two or more smaller implants may be inserted between the vertebral bodies V1, V2. The present embodiments are, therefore, to be considered in all respects as illustrative and not restrictive, and all changes coming within the meaning and equivalency range of the appended claims are intended to be embraced therein.

What is claimed is:

1. A device for insertion between vertebral members in a patient, the device comprising:

first and second end members each including a first side and an opposing second side;

an enclosure member that extends around and is attached to each of the first and second end members and forms an interior volume between the end members;

the first end member attached to the enclosure member at a first location and the second end member attached to the enclosure member at a second location that is spaced apart from the first location, the second sides of the first and second end members facing into the interior volume;

the first and second end members positioned within the enclosure member and being spaced from the vertebral members by the enclosure member when the containment device is inserted between the vertebral members;

the enclosure member positionable between a first orientation with the first and second end members in closer proximity and the interior volume being smaller, and a second orientation with the first and second end members spaced a farther distance apart and the interior volume being larger; the enclosure member attached to the first sides of the first and second end members; the first and second end members each being attached to the enclosure member and move apart when the enclosure member moves from the first orientation to the second orientation.

2. The device of claim 1, wherein the enclosure member further includes an opening that extends into the interior volume, the opening is positioned between the first and second end members.

3. The device of claim 1, wherein the enclosure member is constructed from a flexible, impermeable material.

4. The device of claim 3, wherein the enclosure member includes a reinforcing structure that reinforces the flexible, impermeable material.

5. The device of claim 1, wherein the second sides of the first and second end members include recesses that extend away from the interior volume, the recesses including a narrow neck and a wide end section.

6. The device of claim 1, further comprising at least one support member positioned in the interior volume and within the enclosure member, the at least one support member including a first section attached to the first end member and a second section attached to the second end member.

7. A device for insertion between vertebral members in a patient, the device comprising:
   first and second end members each including a first side and an opposing second side;
   an enclosure member that extends around each of the first and second end members and forms an enclosed interior volume between the end members;
   engagement features positioned on the second sides of the first and second end members and being configured to receive a tool, the engagement features being surrounded by the enclosure member and exposed in the interior volume;
   an opening in the enclosure member that extends into the interior volume, the opening positioned between the first and second end members and in proximity to the engagement features;
   the enclosure member positionable between a first orientation with the engagement features of the first and second end members in closer proximity and the interior volume being smaller, and a second orientation with the engagement features of the first and second end members spaced a farther distance apart and the interior volume being larger; the enclosure member attached to the first sides of the first and second end members at positions away from the engagement features.

8. The device of claim 7, wherein the enclosure member is spaced away from the engagement features.

9. The device of claim 7, wherein the first and second end members and the enclosure member have a substantially cylindrical shape in the second orientation.

10. The device of claim 7, wherein the enclosure member is constructed from a flexible, impermeable material.

11. The device of claim 7, further comprising at least one support member positioned in the interior volume and within the enclosure member, the at least one support member including a first section attached to the first end member and a second section attached to the second end member.

12. The device of claim 7, wherein the engagement features each include a back wall opposite from the interior volume and sidewalls that extend between the back wall and the second sides of the support members.

13. A device for insertion between vertebral members in a patient, the device comprising:
   first and second end members each including a first side configured to contact one of the vertebral members and an opposing second side;
   an anchor recess that extends into the second side of the first end member, the anchor recess including a narrow inlet at the second side that leads into an enlarged section positioned away from the second side;
   a flexible enclosure member that is attached to the second sides of each of the first and second end members and forms an enclosed interior volume between the end members;
   the enclosure member positionable between a first orientation with the first and second end members in closer proximity and the interior volume being smaller, and a second orientation with the first and second end members spaced a farther distance apart and the interior volume being larger;
   the enclosure member positioned away from the enlarged section of the anchor recess in the first orientation and positioned within the enlarged section of the anchor recess in the second orientation.

14. The device of claim 13, wherein the anchor recess in the first end member is a first anchor recess and further comprising a second anchor recess in the second side of the second end member, the enclosure member positioned within the second anchor recess in the second orientation.

15. The device of claim 14, wherein the enclosure member is positioned away from the first sides of each of the first and second end members.

16. The device of claim 13, wherein the recess extends into the second side of the first end member a distance less than a thickness of the first end member measured between the first and second sides.

17. The device of claim 13, wherein the first and second end members are separated from the interior volume by the enclosure member.

* * * * *